United States Patent [19]

Munsch

[11] Patent Number: 5,176,615
[45] Date of Patent: Jan. 5, 1993

[54] APPARATUS FOR FOLDING HYGIENIC PRODUCTS

[75] Inventor: Klaus Munsch, Neuwied, Fed. Rep. of Germany

[73] Assignee: Winkler & Duennebier Maschinenfabrik und Eisengiesserei KG, Neuwied, Fed. Rep. of Germany

[21] Appl. No.: 757,674

[22] Filed: Sep. 10, 1991

[30] Foreign Application Priority Data

Sep. 12, 1990 [DE] Fed. Rep. of Germany ....... 4028889

[51] Int. Cl.⁵ .................. B65H 45/16; B41F 13/62
[52] U.S. Cl. .................................... 493/427; 493/444
[58] Field of Search ............... 493/424, 425, 426, 427, 493/428, 429, 430, 431, 432, 433, 444

[56] References Cited

U.S. PATENT DOCUMENTS

| 879,510 | 2/1908 | Bechman | 493/427 |
|---|---|---|---|
| 1,536,581 | 5/1925 | Halliwell | 493/427 |
| 1,578,436 | 3/1926 | Herb | 493/427 |
| 1,684,901 | 9/1928 | Wood | 493/352 |
| 3,337,211 | 8/1967 | Bilane | 493/357 |
| 3,578,311 | 5/1971 | Wood et al. | |
| 3,994,486 | 11/1976 | Nystrand | 493/427 |
| 4,053,150 | 10/1977 | Lane | |
| 4,084,391 | 4/1978 | Williams, Sr. et al. | |
| 4,717,375 | 1/1988 | Lundmark | 493/360 |

FOREIGN PATENT DOCUMENTS

| 0005671 | 1/1985 | European Pat. Off. | |
|---|---|---|---|
| 1811840 | 4/1960 | Fed. Rep. of Germany | |
| 1246767 | 8/1967 | Fed. Rep. of Germany | |
| 2242577 | 3/1974 | Fed. Rep. of Germany | |
| 2323433 | 11/1975 | Fed. Rep. of Germany | |
| 3528634 | 2/1987 | Fed. Rep. of Germany | |
| 3614984 | 11/1987 | Fed. Rep. of Germany | |
| 3806361 | 4/1989 | Fed. Rep. of Germany | |
| 225306 | 12/1924 | United Kingdom | 493/427 |
| 255352 | 7/1926 | United Kingdom | 493/427 |
| 1377089 | 12/1974 | United Kingdom | |

Primary Examiner—William E. Terrell
Attorney, Agent, or Firm—W. G. Fasse

[57] ABSTRACT

An apparatus for folding hygienic products, especially soft, oblong articles having a small thickness, has a folding tool that is driven by a drive mechanism providing two rotary motions one superimposed on the other and interlinked in such a way that the folding tool applies pressure along an intended fold-line, whereby the article being folded is pushed while being folded in a transport direction. The interlinking of the two superimposed motions assures a quiet, smooth, yet high speed run of the folding tool and its drive mechanism. By pushing the article along its fold-line into a gap or take-up channel, a positive folding of the article is assured, whereby already folded portions are prevented from unfolding again.

16 Claims, 9 Drawing Sheets

APPARATUS FOR FOLDING HYGIENIC PRODUCTS

FIELD OF THE INVENTION

The invention relates to a folding apparatus for the folding of hygienic products, especially soft, oblong articles having a small thickness, such as, for example, diaper-pants, sanitary napkins, and similar articles.

BACKGROUND INFORMATION

Methods and apparatus of the above type are generally known and are described, for example, in the following German Patent Publications: (DE) 3,528,634 Al, (DE) 3,614,984 Al, and (DE) 3,806,361 Cl. The articles to be packaged are first folded several times with the help of rollers and suction air and then packaged, whereby the articles may additionally be rotated or turned over.

German Patent Publication 1,246,767 (Kuehne) discloses a folding and collecting mechanism for rotary printing machines in which the components which control the folding knives are moving uniformly on circular paths, whereby wear and tear causing motions are avoided and those mass accelerations and decelerations which reduce output are minimized or possibly avoided. Gear meshing play and bearing play is to be minimized to increase the folding precision. For this purpose Kuehne provides a folding cylinder with a circumference suitable to carry three sheets to be folded. The cylinder carries folding grooves and inside the cylinder there is a folding knife carrier with three folding knives. The knife carrier rotates eccentrically in the cylinder, whereby the folding knives are mounted on rotatable spindles to control the motion of the folding knives by planetary gears which revolve around a sun gear that is drivable and stoppable. Crank drives are also shown.

The working speed of the known folding machines is relatively high, but it is not high enough in many instances. Especially since components other than the folding components of the known production machines could be run with a higher hourly output, the folding components of a production line form a bottleneck that substantially affects the working speed of the entire production line.

OBJECTS OF THE INVENTION

In view of the above it is the aim of the invention to achieve the following objects singly or in combination:
to provide a method and apparatus for the folding of hygienic articles, which allow for an increased working speed of the folding operation;
to optimally increase the motion efficiency of the folding tools by minimizing the extent of these motions and by avoiding or at least reducing unnecessary motions;
to apply pressure to the article to be folded along a folding line and to move or shift the article while such linear pressure is applied to make the fold along the folding line;
to minimize as much as possible the centrifugal and mass or rather inertia forces to achieve a high speed yet quiet operation of the motions of folding tools in a folding apparatus for thin flat articles; and
to provide an apparatus in which folding tools are so controlled in their motion that each tool presses on the article along a folding line extending perpendicularly to a feed advance direction of the article thereby shifting the article into a take-up channel or gap along the entire line.

SUMMARY OF THE INVENTION

The foregoing objects have been achieved according to the invention by a folding mechanism which is characterized by a folding tool controlled in its motion by a drive system which superimposes a first rotary motion on a second rotary motion for operating the folding tool. At least one motion direction detecting element is interposed between the components that perform the first rotary motion and the second rotary motion. The motion direction determining element mainly makes sure that one rotary motion is opposite to the other rotary motion to thereby assure a smooth and quiet run. The motion direction determining element may be an intermediate counterrotating gear wheel in a planetary gear system. The same function is achieved by a gear belt drive or a chain drive between the components that generate the first and second rotary motions. In another embodiment a double crank drive also achieves a very quiet, yet high speed run.

According to the invention it is possible to fold a soft, oblong article into two or three layers having its ends folded on top of one another. The pressure action at the fold line perpendicular to the transport direction of the article to be folded, permits generating support pressures which are effective in the transport direction of said article. The support pressures secure the end of the article which is prefolded in a first folding step and then oppose the material-dependent forces that work in an unfolding direction. As a result, very high working speeds are achieved.

The apparatus according to the invention comprises a folding tool that contacts the moving, oblong article along the folding line and pushes the article perpendicularly to the direction of article movement, in a folding manner in a direction perpendicularly into a take-up channel, or rather, into a gap. Preferably, a drive mechanism, such as a gear drive acts as the drive mechanism for the folding tool that is movable perpendicularly to the direction of movement of the article to be folded. The gear drive comprises a planetary gear train having a stationary sun wheel, an intermediate gear wheel, as well as a planetary gear to control the folding tool motions. The intermediate gear makes sure that the planetary gear rotates in a counter direction relative to the direction of rotation of a gear carrier member. Instead of an intermediate gear a gear belt or chain drive may be used. In another embodiment the motion of the folding tool is controlled by a crank drive.

The form and shape of the free or operating end of the folding tool and the type of movement of the folding tool preferably add to the creation of lateral pressures and forces, that oppose any opening tendency of the already prefolded article portion.

BRIEF DESCRIPTION OF THE DRAWINGS

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figure 1:
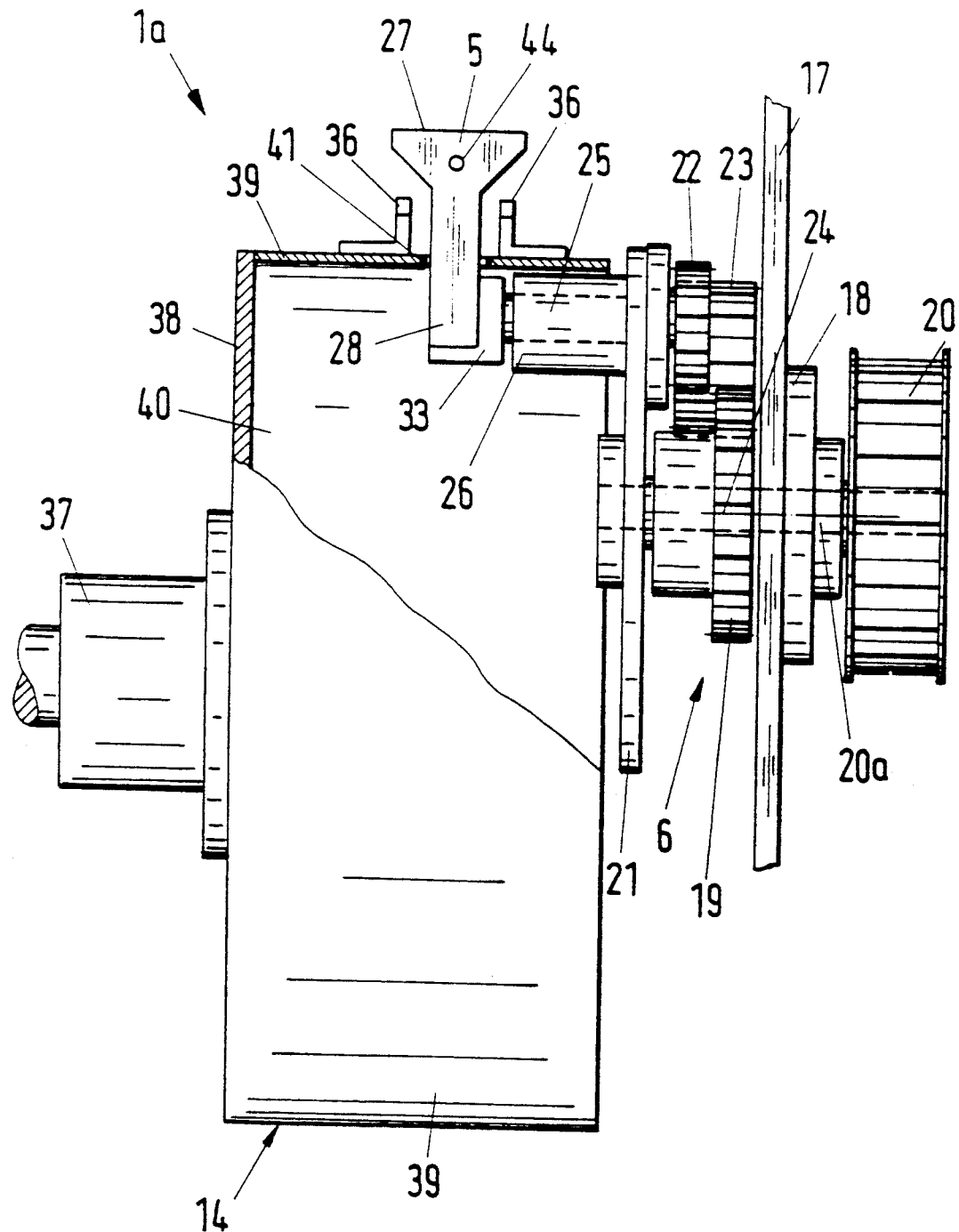
FIG. 1 is a side view, partially in cross-section, of the essential components of the present folding mechanism.

FIG. 1 shows an apparatus 1, 1a referred to as folder for folding hygiene products, especially soft, oblong articles 2 having a small thickness, to which pressure is applied along the intended folding line 3. With the pressurized line leading in a feed advance direction, the articles are then pushed while being folded into a take-up channel or gap 4. Each folder 1, 1a comprises a folding tool 5 and a drive mechanism for the folding tool 5, in the form of a gear drive 6, as well as transport belts 7 and 8, that run over guide rollers G1, G2 for forming a take-up channel or gap 4 as shown in FIG. 2.

Figure 2:
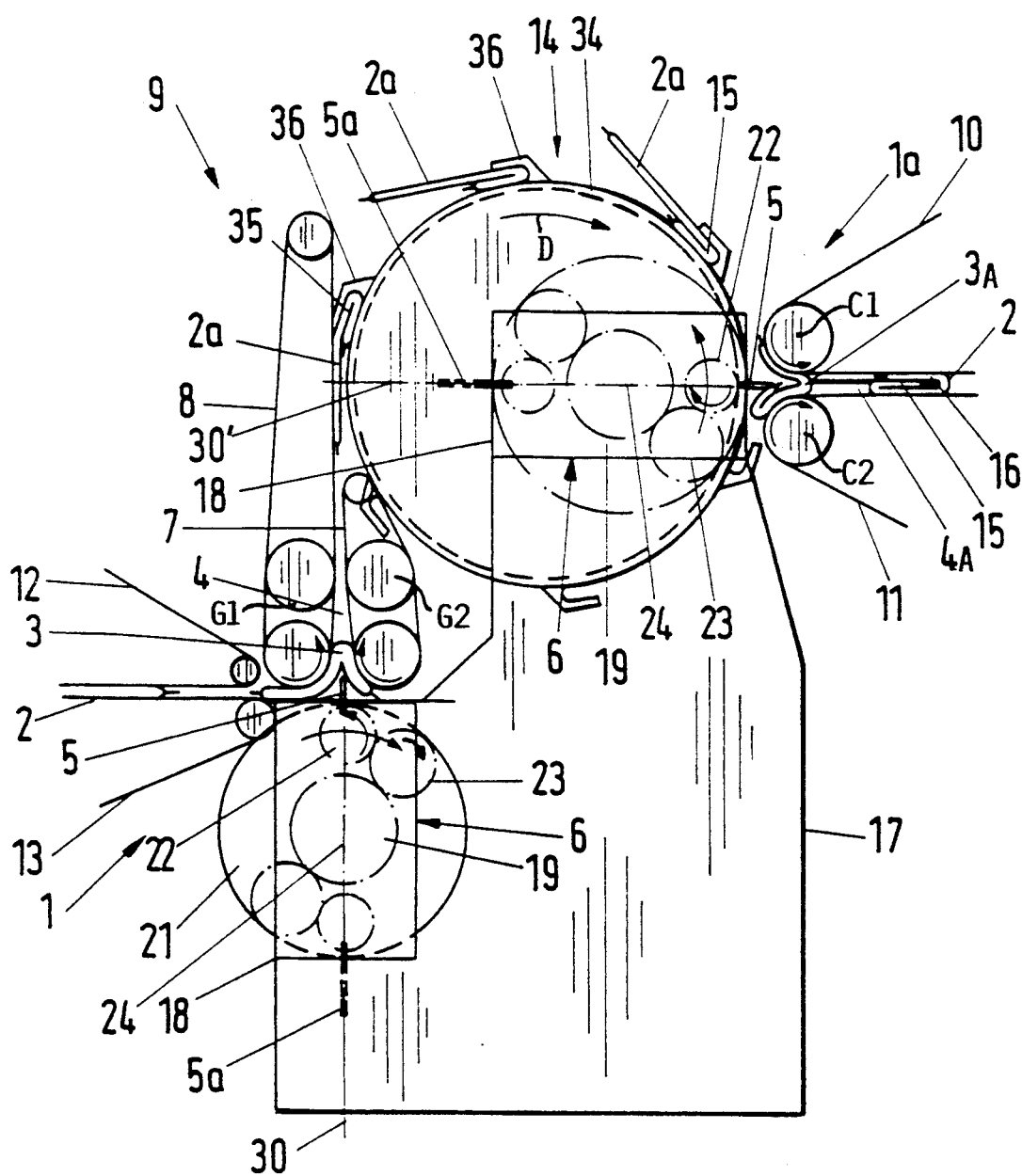
FIG. 2 is a front view, on a smaller scale, compared to FIG. 1, of two folding mechanisms according to FIG. 1 arranged in sequence to make two folds in a flat article to form a three layer article.

According to FIG. 2, two folders 1 and 1a belong to a folding station 9. The folder 1a also comprises two transport belts 10 and 11, that run over guide rollers C1, C2 for forming take-up gap 4. Further transport belts 12 and 13 are provided, in order to guide the article 2 to be folded, first to the folder 1, before the transport bands 7 and 8 extending vertically and forming the first gap 4, guide the once folded article 2a to a guide- and folding-drum 14 cooperating with the second folder 1a. The drum in cooperation with the folder 1a performs the second folding, so that the ends 15 and 16 of the article 2a lie one on top of the other.

The drive mechanism for both of the folders 1 and 1a, according to FIGS. 1 and 2, comprises a wheel gear drive in the form of a planetary gear drive 6, including a stationary sun wheel 19 mounted to a mounting plate 18, which is adjustable in its position relative to a supporting frame 17. The gear drive 6 further comprises a carrier 21, a planetary gear wheel 22, and a counterrotating intermediate gear wheel 23. The carrier 21 is arranged on a shaft 20a rotatably mounted to the supporting frame 17 and is driven by a drive gear wheel 20. The planetary gear wheel 22 and the counterrotating intermediate gear wheel 23 that meshes with the sun wheel 19 and with the planetary wheel 22 are rotatably mounted on the carrier 21 which is preferably disk-shaped.

According to one of the preferred example embodiments, the ratio between the number of teeth on the planetary gear wheel 22 to the number of teeth on the sun wheel 19 is 1:2. The number of teeth on the intermediate gear wheel is selectable. However, the intermediate gear wheel has been found to be important for a smooth, quiet run. Therefore, when the drive gear wheel 20 rotates the carrier 21 through the shaft 20a, then the planetary gear 22 and the intermediate gear wheel 23 circle around the still standing sun wheel 19, whereby, further, the planetary gear 22 rotates counterclockwise when the carrier 21 rotates clockwise, as shown in FIG. 1. Gear 23 determines the motion direction.

According to the illustration in FIGS. 1 and 2, the planetary gear 22, which does not mesh with the sun wheel 19, is arranged axially displaced relative to the sun wheel 19. With respect to the orbit, the planetary gear 22 is also displaced laterally next to the intermediate gear wheel 23. The intermediate gear wheel 23 meshing with the planetary gear 22 and with the sun wheel 19, has an axial width at least equal to the width of the sun wheel 19 plus the width of the planetary gear 22. Therefore, it is possible to arrange the planetary gear 22 and the intermediate gear wheel 23 near to the shaft 20a, or rather, near to the axis 24 of the sun wheel 19. The axis 24 of the sun wheel 19 is also the rotational axis of the shaft 20a which thus rotates with the carrier disk 21 about the axis 24.

The folding tool 5 is supported on the carrier 21 to freely rotate about an arm 25. The planetary gear 22 controls the motion of the folding tool. The arm 25 is a shaft, rotatably supported in the carrier 21 for connecting the planetary gear 22 with the folding tool 5 and for transmitting the rotation movement of the planetary gear 22 to the folding tool 5. A sleeve 26 forms a bearing for the shaft 25 and thus for the planetary gear 22 and for the folding tool 5 on the carrier 21.

Figure 5:
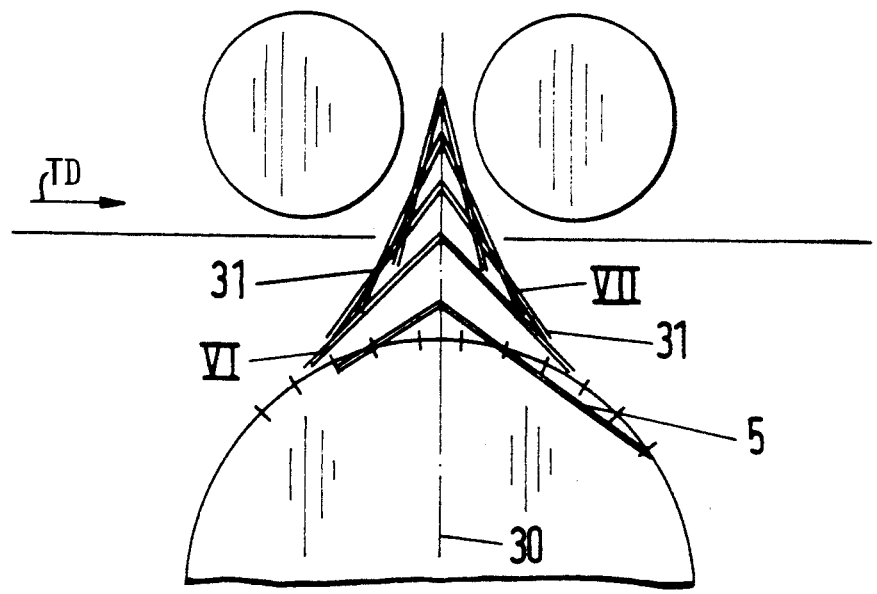
FIG. 5 is a motion study or motion sequence of a folding tool working symmetrically relative to a folding gap or channel formed by two rollers.
Figure 6:
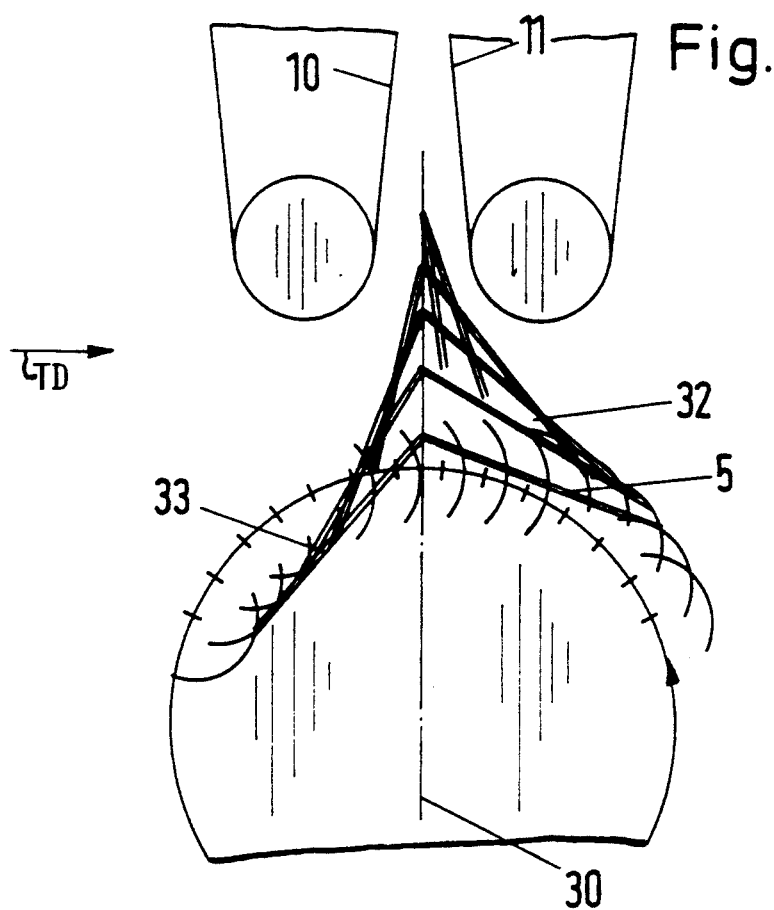
FIG. 6 is a motion study or motion sequence of a folding tool working asymmetrically relative to a folding gap or channel.
Figure 7:
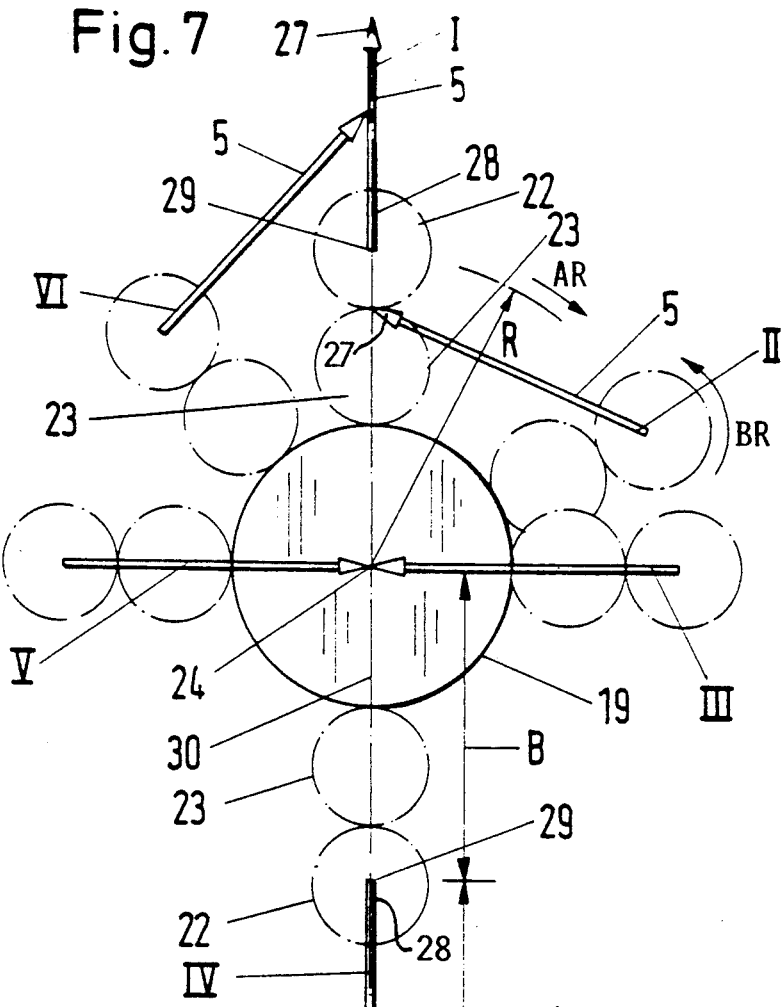
FIG. 7 illustrates schematically the course of motion of the present folding tool under the control of a planetary gear train including a sun wheel and an intermediate gear wheel.

The motions of the folding tool 5 generated by the sun wheel 19, the planetary gear 22, and the intermediate gear wheel 23 and thus the motions of the free end 27 and of the shaft end 28 of the tool 5 are shown in FIGS. 5, 6, and 7, whereby the following applies.

When the planetary gear 22, as shown in FIG. 7, moves with its rotation axis 29 in a clockwise direction along a radius R in the direction of the arrow AR around the axis 24 of the sun wheel 19, then the planetary gear 22 rotates, because of the intermediate gear wheel 23 of the invention, in a counterclockwise manner in the direction of the arrow BR. Because of the preferred gear ratio of 2:1 between the sun wheel 19 and the planetary gear 22, the latter rotates counterclockwise by the same angle magnitude as that at which the gear 22 travels clockwise around the sun wheel 19. Therefore, the folding tool 5, which is controlled by the planetary gear 22, completes one full counterclockwise rotation during one full revolution of the planetary gear 22, and the rotational motion of the planetary gear 22 is superimposed on said counterclockwise rotation of the tool 5. Hence, the folding tool 5 tips out of the position I, corresponding to its highest folding position, during the pulling back, first to the left into the position II and then further into the position III according to FIG. 7, until the tool reaches the furthest pulled back position IV. In position IV the free end 27 of the folding tool 5 faces in a direction opposite to that it faced in the position I. During the further revolution of the planetary gear 22, the folding tool 5 lifts again, passes through the position V and meets the article 2 to be folded at about the position VI. The position VI in FIG. 7 corresponds to a mirror-image position, not shown in FIG. 7, that lies to the right of the central axis 30 relative to which the motions are viewed, and which mirror-image position occurs during the pulling back of the folding tool from position I.

The folding tool 5 defines, by itself, with its free end 27 and with its shaft end 28, an envelope curve 31 that is partially shown in FIG. 5, in the area of the fold-line 3 and relative to the central axis 30 during forward movement and during backward movement. This envelope curve 31 makes it apparent that the folding tool 5 exerts changing forces on the article 2 to be folded, not only perpendicularly to the feed-in transport direction TD, but also in the transport direction TD, since the tool 5 moves out of the position VI left of the beginning of the folding process into the position VII (FIG. 5) to the right of the central motion axis 30 at the end of a folding process.

The envelope curve 31 in FIG. 5 represents the motion course or path of a folding tool 5 working symmetrically to the motion axis 30. In this instance the tool 5 extends radially to its own axis of rotation. FIG. 6 shows an envelope curve 32 of an asymmetrically working folding tool 5. The asymmetrical envelope curve 32 is achieved when the folding tool 5 is mounted off-center relative to its own axis of rotation on an arm 25 carrying the off-center mounted tool.

A symmetrically effective arrangement of the folding tool 5 with an envelope curve 31 as shown in FIG. 5 is advantageous, if the folding tool executes a first fold on an elongated article 2 in the first folder 1 of the folding station 9, as shown in FIG. 2. The asymmetrically effective envelope curve 32 and the off-center arrangement of the folding tool 5 are advantageous in the production of the second fold 3a in the folder 1a of the folding station 9, because here the folding tool 5 not only pushes the once folded article 2a into the gap 4a, but the tool should also prevent the prefolded end 15 from opening and from being pulled out of the folded portion of the article when the folding tool 5 is pulled back.

The folding tool 5 can be attached with its shaft end 28 to the shaft 25 by means of a connecting member 33 to extend radially relative to its own axis 29 of rotation to provide the symmetrical motion according to FIG. 5. The motion of FIG. 6 is achieved by a leading position of the tool relative to its own rotational direction. In the leading tool position illustrated in FIG. 6, the folding tool 5 reaches the position I of FIG. 7 even before the rotation axis 29 of the planetary gear 22 passes through the motion axis 30. When the tool 5 takes up a trailing position relative to its own rotational direction, the folding tool 5 is eccentrically arranged on the shaft 25 so that its rotation axis 29 which is also the rotation axis of the planetary gear 22 and of the shaft 25 crossed over the motion axis 30 before the folding tool 5 reaches an alignment position with or in a position parallel to the motion axis 30. Preferably, the folding tool 5 is adjustably mounted so that it executes an optimal motion corresponding to what is required, either leading or trailing the passage of the axis 29 through the axis.

As shown in FIG. 7, it is especially advantageous if the distance A, from the rotation axis 29 of the planetary gear 22, or rather of the shaft 25, to the free end 27 of the folding tool 5, is as long as the distance B from the rotation axis 29 of the planetary gear 22 to the axis 24 of the sun wheel 19. The free end 27 of the folding tool 5, which is symmetrically arranged to the axis 29, then moves along the movement axis 30, while the planetary gear 22 completes one revolution.

The device 1a in the folding station 9 of FIG. 2 also comprises, compared to the device 1, a guide- and folding drum 14. The partly folded article 2a, coming from the device 1 with its fold 35 leading, runs onto the circumference 34 of said drum 14. The guide- and folding-drum 14 has finger-like holding elements 36 arranged in pairs in the direction of the drum circumference for holding the article 2a. The transport bands 7 and 8 push the articles 2a individually into the space between the finger-like holding elements 36 and the circumference 34 of the drum 14.

The guide- and folding-drum 14 sits freely cantilevered on a drive shaft 37 and comprises a drum bottom 38 and a cylindrical wall 39, which is open toward the gear drive 6, (see FIG. 1).

The arm 25, or rather the shaft 25 that carries the folding tool 5 and the sleeve bearing 26 that is arranged on the carrier 21 for mounting the gear drive 6, reach inside a space 40 of the guide- and folding-drum 14 from the open drum side opposite the drum bottom 38. The folding tool 5 sticks out at a 90° angle from the arm 25, that is to say it stands radially or essentially radially to the rotation axis 29 of the planetary gear 22.

Almost the entire motion of the folding tool 5 according to FIG. 7 takes place inside the space 40 of the guide- and folding-drum 14. Only for the direct folding operation does the folding tool 5 reach out with its free end 27 through openings 41 while its other end 28 and the arm 25, remain in the inside of the guide- and folding-drum 14.

One opening 41 is arranged on the circumference 34 of the guide- and folding-drum 14 for each group of finger-like holding elements 36.

Figure 3:
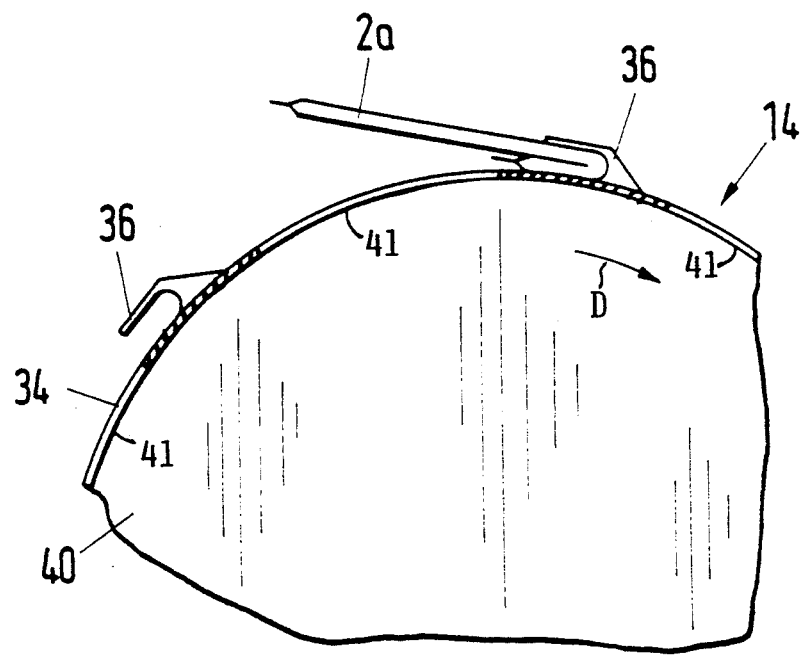
FIG. 3 shows an enlarged view of a guide and folding drum of FIG. 2 arranged between the two folding mechanisms.
Figure 4:
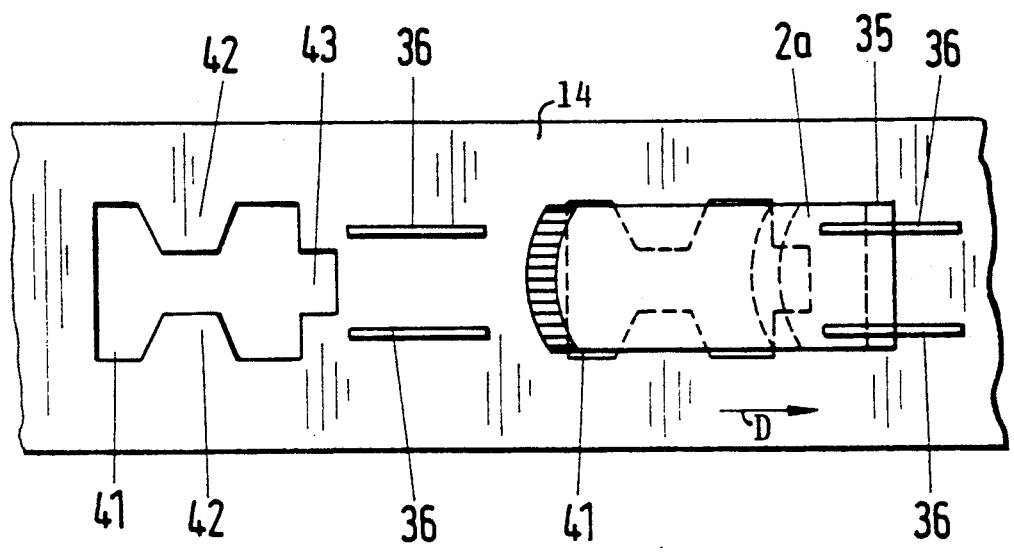
FIG. 4 is a partial view of the developed projection of the folding drum circumference, according to FIG. 3.

As shown in FIGS. 3 and 4, one opening 41 is positioned, with regard to the direction D of rotation of the drum 14, behind the finger-like holding elements 36 that hold the once folded article 2a. The openings 41 have protrusions 42 at half-length that face each other and a recess 43 that faces the finger-like holding elements 36, which allow for the smallest possible opening area for the opening 41, when taken with regard to the T-form of the folding tool 5 shown in FIG. 1 and with regard to the motions of said tool 5 corresponding to the envelope curves 31 and 32 of FIGS. 5 and 6. A minimal opening area is desired to prevent dust and similar contaminations from entering into the inside 40 of the guide- and folding-drum 14.

In operation, the folder 1 works with its folding tool 5 pointing vertically upward at the time of starting the folding pressure while the free end 27 of the folding tool 5 moves along the, in FIG. 2 vertically positioned, central motion axis 30. In the folder 1a, the folding tool 5 works horizontally and moves with its free end along the horizontally lying axis 30'. Shown only by a dotted line 5a is the folding tool with its planetary gear and the intermediate gear wheel, in FIG. 2, in the position IV shown in FIG. 7. Position IV is reached after a half orbit, when the free end 27 of the folding tool 5 has moved the furthest away from the fold-line 3.

The guide- and folding-drum 14 forms a housing for mounting and protecting the folding tool 5 and the corresponding components of its drive mechanism.

In order to maintain on the free end 27 of the folding tool 5, not only pressure forces that work in the direction of the movement axis 30, compressed air may be effective laterally of the free end 27 as an auxiliary to the pressure forces exerted by the tool 5. For this purpose a blast or below nozzle 44 is located laterally on the free end 27 of the folding tool 5 as shown in FIG. 1. The nozzle 44 is suitably connected to an air compressor through a control valving mechanism in a manner not shown in the Figures. Such valving mechanisms are known in the art.

Besides, a spring biased pressure piece may also be arranged laterally on the free end 27 of the folding tool 5, in order to produce the desired lateral pressures and forces for enhancing the folding operation. As shown in FIG. 1, the free end 27 of the folding tool 5 preferably has an approximately T-shaped configuration.

Figure 8:
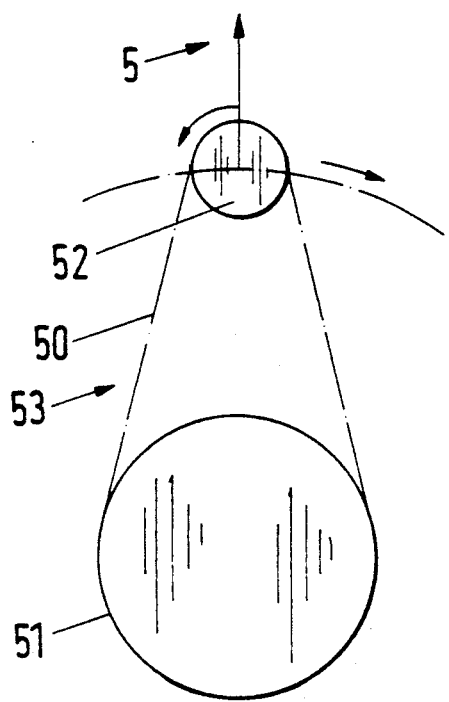
FIG. 8 shows a chain- or gear-belt drive instead of the intermediate gear wheel for the present folding tool.

While in the example embodiment of FIGS. 1 to 7, the counterclockwise movement of the planetary gear 22 is produced by the intermediate gear wheel 23 which thus determines the motion direction, in FIG. 8 this counterclockwise movement is produced by a rotation transmitting member 50, such as a gear belt or a sprocket chain that encircles a still-standing sun wheel 51 and an orbiting planetary wheel 52 to thus determine the motion direction. The same components as in the first described example embodiment work to produce the orbiting motions of the planetary gear 52. Thus, the drive gear of FIG. 8 is a belt or chain drive 53, including the wheels 51, 52 cooperating with a gear belt or similar device, for example, a sprocket chain.

Figure 9:
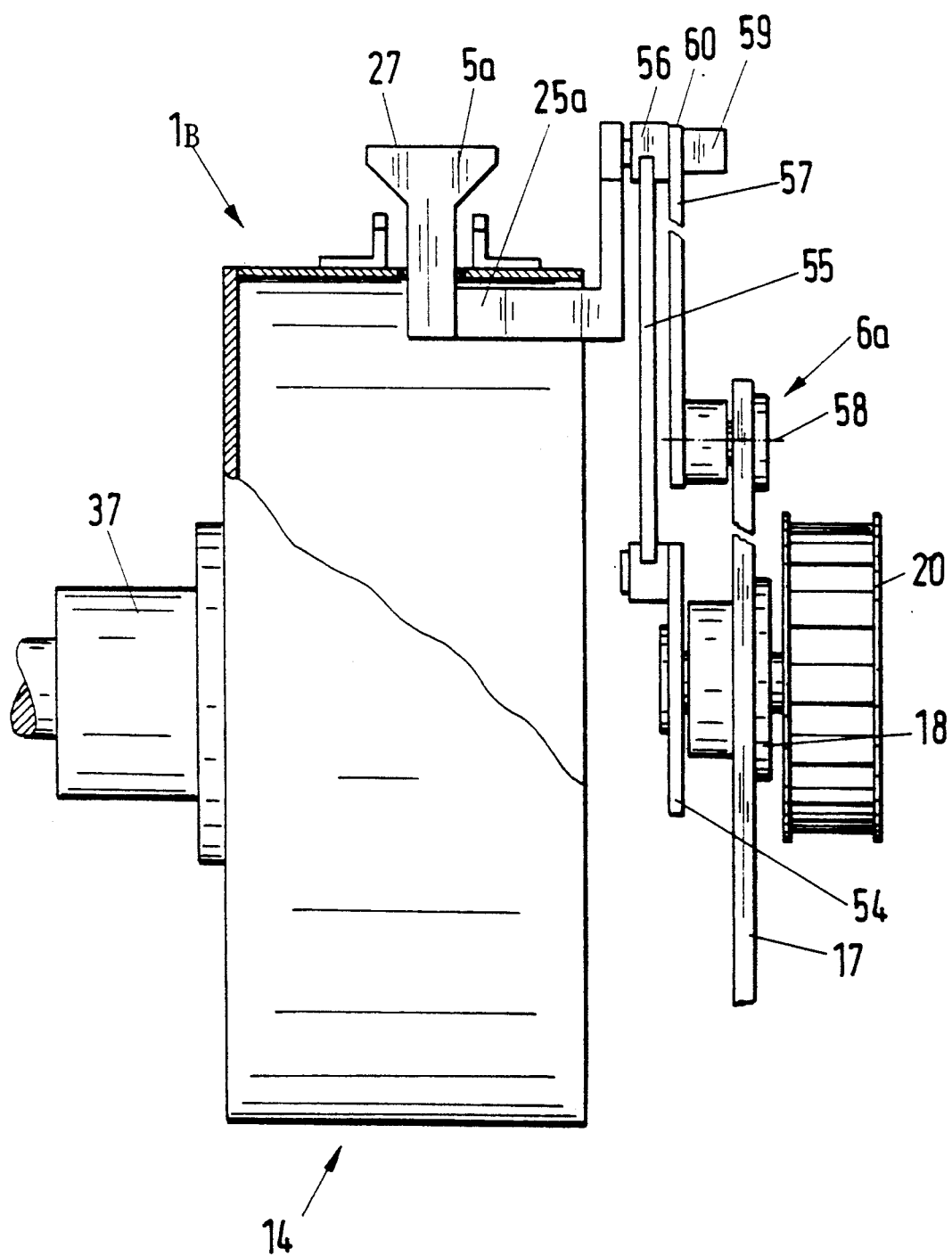
FIG. 9 is a view similar to that of FIG. 1, but showing a modified example embodiment with two crank drives instead of a planetary gear train.
Figure 10:
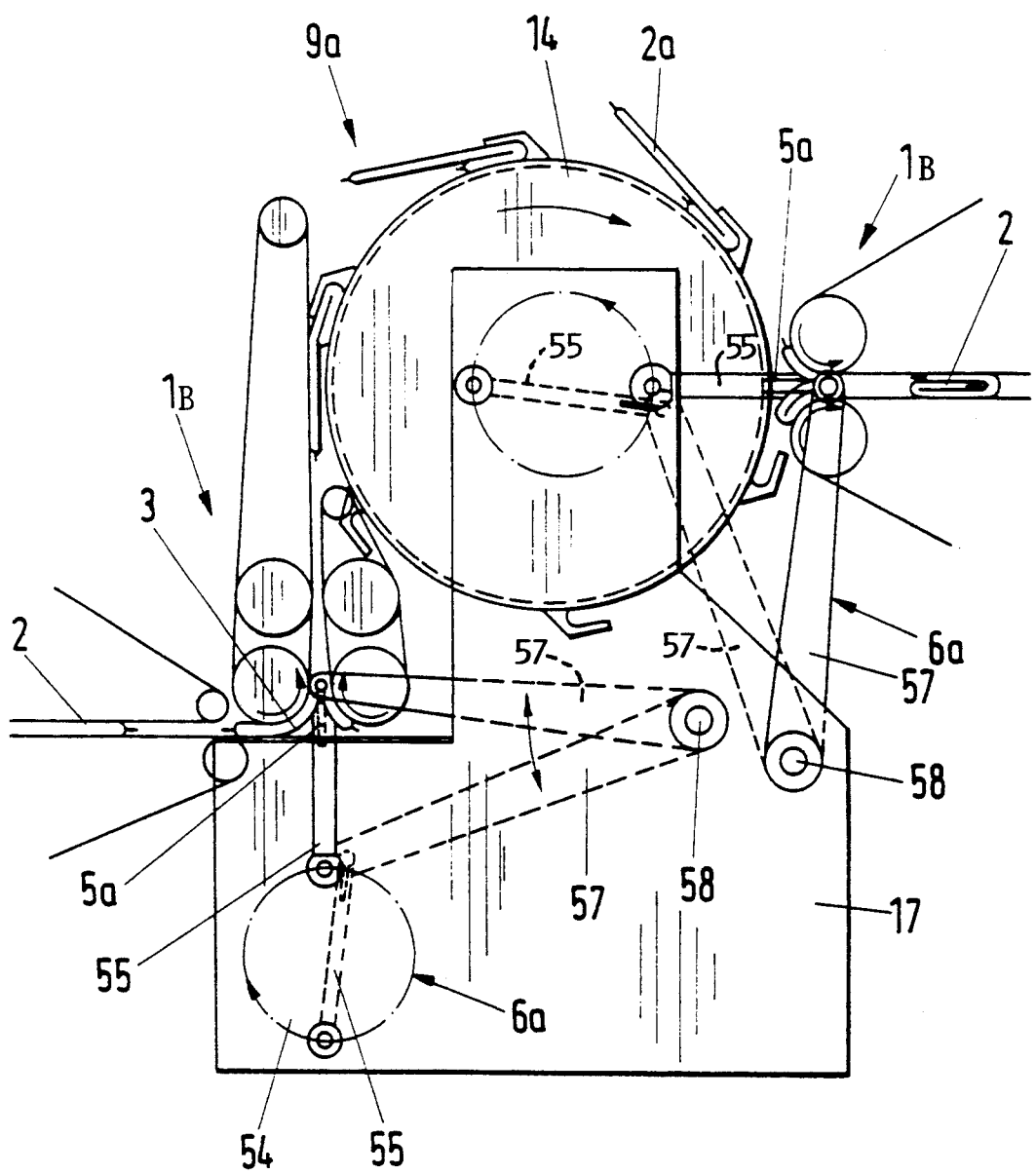
FIG. 10 is a view similar to that of FIG. 2, with the crank drives according to FIG. 9.

Both FIGS. 9 and 10 show a further example embodiment of a folder 1b, wherein a crank gear drive 6a has replaced the planetary gear drive 6, as the drive mechanism for the folding tool 5. The various components of the folder 1b of FIGS. 9 and 10 carry the same reference numbers if these components perform an identical function as respective components of the folder 1 in FIGS. 1 to 7. As far as the components are merely similar or perform a similar function, they have the same reference numbers, but with an index "a", e.g. crank drive 6a.

The crank drive 6a comprises a drive wheel 20 that is rotatably mounted in a supporting frame 17 by means of an adjustable carrier plate 18. The wheel 20 drives a crank disk 54. One end of a crank arm 55 is pivoted on the crank disk 54 to be freely rotatable. The other end of the crank arm 55 facing away from the crank disk 54 is pivoted to a guide arm 57. FIG. 10 shows the crank arm 55 and the guide arm 57, respectively, in their lowermost or uppermost work positions, whereby the uppermost work position further defines the end point of the movement of the folding tool 5 in the folding process. The guide arm 57 is relatively long and pivotally mounted to the supporting frame 17. The pivot or journal axis 58 of the guide arm 57 is at about the same level as the article 2 to be folded during the folding operation, see FIG. 10.

The folding tool 5a is connected by an angled arm 25a to the free end 56 of the crank arm 55 as shown in FIG. 9. If this connection is rigid, the folding tool 5a moves in absolute synchronization with the crank arm 55. However, if the folding tool 5a is rigidly connected by its arm 25a and a bearing pin 59 to the free end 60 of the guide arm 57, then its motions are synchronized with those of the guide arm 57. In this latter case, the free end 27 of the folding tool 5a, corresponding to the position of the journal axis 58 of the guide arm 57, dips more or less diagonally along the fold-line 3 into the article 2 to be folded and leaves it again in the same direction.

FIG. 10 shows a folding station 9a with two folders 1b, each having respective crank drives 6a with crank disks 54, crank arms 55 and guide arms 57.

Yet another example embodiment is shown in FIGS. 11 and 12, wherein again the same components have identical reference numbers, and adapted or modified components carry the index "b".

A drive wheel 20 that is freely supported for rotation in a supporting frame 17 and that drives a crank disk 54, is again used as the drive mechanism. One end of the crank arm 55 is journalled to the crank disk 54 and its other end 56 is pivoted or journalled to a sliding carriage 61. The sliding carriage 61 is guided along a linear guide rail 62, so that the free end 56 moves along the linear guide rail 62 during each revolution of the crank disk 54.

An angled arm 25b carries the folding tool 5b and is connected to the free end 56 of the crank arm 55. The arm 25b may further be rigidly connected either with the free end 56 of the crank arm 55 or with the sliding carriage 61. The free end 27 of the folding tool 5b completes either linear motions parallel to the linear guide rail 62 or journalling motions superimposed on the linear motions corresponding to the motions of the crank arm 55, with each revolution of the crank disk 56.

Figure 11:
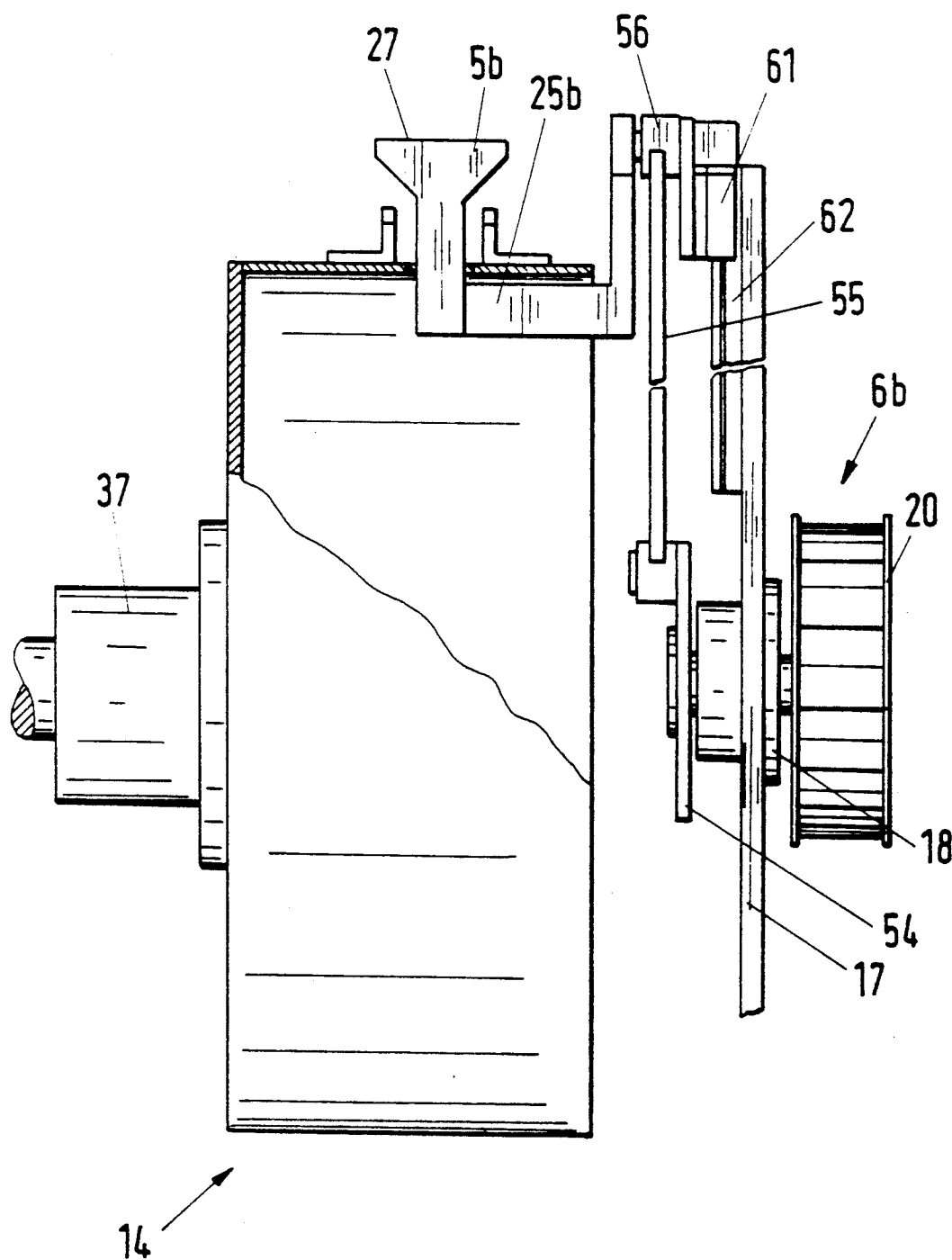
FIG. 11 is a view similar to that of FIG. 9 of a further example embodiment with a crank drive and a linear guide.
Figure 12:
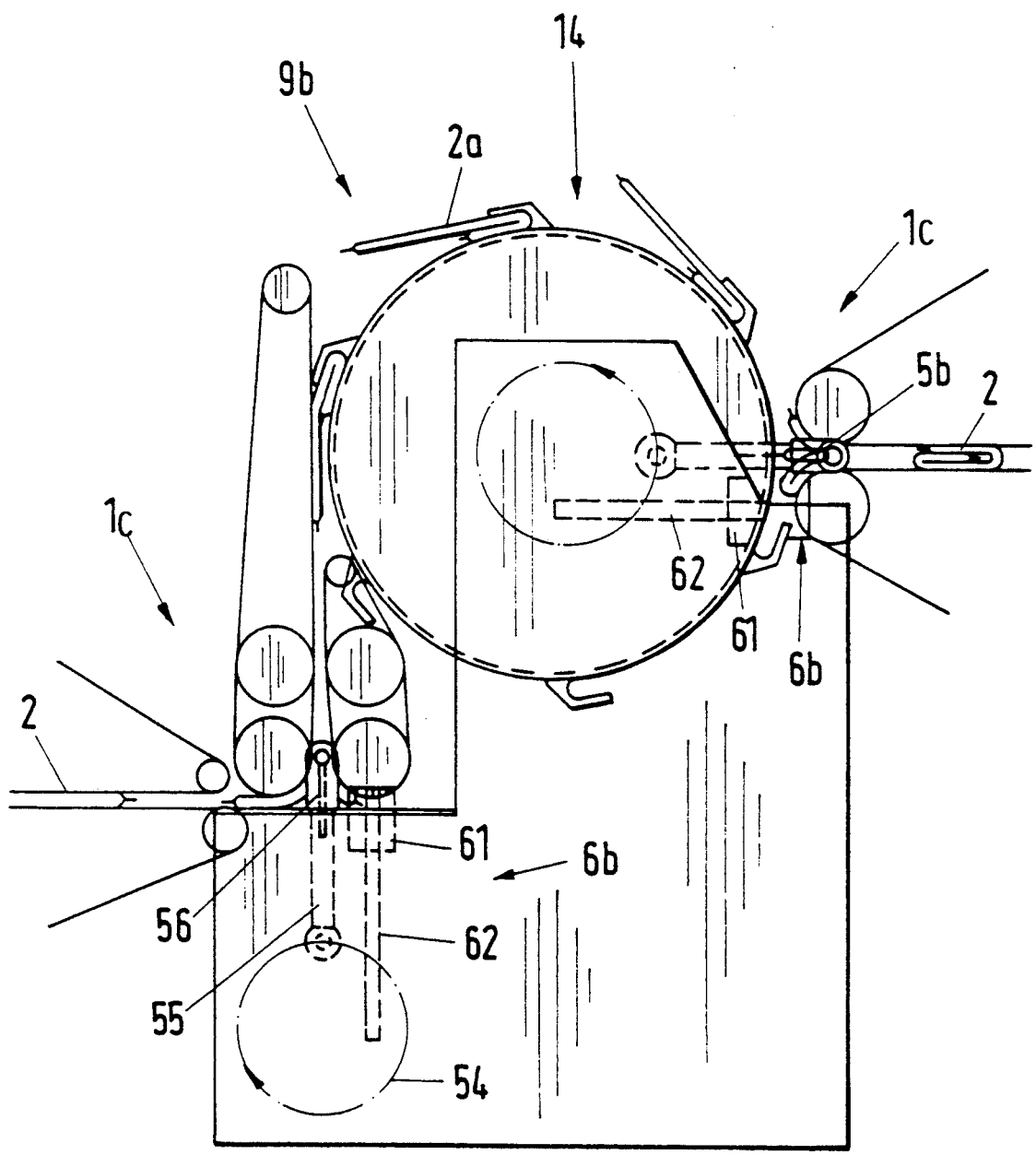
FIG. 12 is a view similar to that of FIG. 10, with crank drives according to FIG. 11.

The folding station 9b shown in FIG. 12 comprises two folders 1c as in FIG. 11, whereby both folders 1c are equipped with crank drives 6b that have crank disks 54, crank arms 55, and linear guide rails 62. Merely the position of the crank gear 6b, or rather of the linear guide rail 62 is different and in one case vertically arranged and in the other case horizontally arranged. Correspondingly, the folding tool 5b is vertically movable to produce the first fold and horizontally movable to produce the second fold.

Although the invention has been described with reference to specific example embodiments, it will be appreciated, that it is intended to cover all modifications and equivalents within the scope of the appended claims.

What I claim is:

1. An apparatus for folding flat, thin articles moving in a feed direction, comprising a stationary frame (17), means forming a folding gap (4), a folding tool (5, 5a, 5b) for performing a composite folding motion to fold said articles into said folding gap, drive means (6) for producing a composite motion for said folding tool, said drive means (6) comprising a stationary sun gear (19) mounted to said stationary frame (17), a planetary gear (22) connected to said folding tool and mounted for rotation in said stationary frame, an intermediate gear (23) interposed between said stationary sun gear (19) and said planetary gear (22), a driven shaft (20a) having a first rotation axis (24) mounted for rotation in said stationary frame (17) centrally through said stationary sun gear (19), a carrier (21) for supporting said planetary gear (22) on a second rotation axis (29) and said intermediate gear on its rotation axis, said carrier being mounted for rotation to said driven shaft (20a) about said first rotational axis, wherein said intermediate gear (23) meshes with said stationary sun gear (19) and with said planetary gear (22), mounting means (25, 26) for rotatably mounting said folding tool to said carrier (21) for controlling said composite motion of said folding tool by said planetary gear (22) for folding an article into said gap (4).

2. The apparatus of claim 1, wherein said mounting means (25, 26) for said folding tool comprise a bearing bushing (26) secured to said carrier (21) and a shaft (25) rotatably supported in said bearing bushing (26) for permitting said composite motion of said folding tool.

3. The apparatus of claim 1, further comprising drive means (20) connected to said driven shaft (20a) for rotating said carrier (21) through said driven shaft (20a), and wherein said carrier (21) is a disk, mounted on said driven shaft.

4. The apparatus of claim 1, wherein said stationary sun wheel has a gear ratio of 2 to 1 to said planetary gear (22).

5. The apparatus of claim 1, wherein said planetary gear (22) is arranged axially displaced relative to said sun gear (19), and wherein said intermediate gear (23) has an axial width at least equal to an axial width of said sun gear (19) and of said planetary gear (22), so that said intermediate gear (23) meshes with said sun gear (19) and with said planetary gear (22).

6. The apparatus of claim 1, wherein a radial spacing (A) between said second rotation axis (29) of said planetary gear (22) and a free end (27) of said folding tool (5) is equal to a radial spacing (B) between said second rotation axis (29) and said first rotation axis (24) of said driven shaft (20a).

7. The apparatus of claim 1, further comprising a guide and folding drum (14), a drive shaft (37), said guide and folding drum (14) being mounted in a cantilevered manner on said drive shaft for rotation, said guide and folding arm being open toward said drive means (6) for cooperation with said folding tool.

8. The apparatus of claim 7, wherein said guide and folding drum (14) comprises a drum bottom (38) and a cylindrical wall (39), said cylindrical all (39) having at least one opening (41) therein through which said folding tool (5) reaches radially outwardly with its free end (27).

9. The apparatus of claim 8, further comprising at least one article holding finger (36) secured to an outer surface of said cylindrical wall of said guide and folding drum (14).

10. The apparatus of claim 9, wherein said opening (41) in said cylindrical wall (39) is positioned behind said at least one holding finger as viewed in the rotation direction of said guide and folding drum.

11. The apparatus of claim 1, wherein said folding tool (5) comprises an approximately T-shaped configuration.

12. The apparatus of claim 1, wherein said folding tool (5) comprises a blow nozzle (44) near its free end for blowing against said article.

13. The apparatus of claim 1, further comprising a mounting plate (18) for said stationary sun gear (19), said mounting plate being secured to said stationary frame (17) for adjusting a position of said sun gear (19) on said stationary frame (17).

14. The apparatus of claim 1, wherein said drive means for said folding tool comprise at least one crank drive.

15. The apparatus of claim 1, wherein said folding tool is arranged to perform a folding motion substantially vertically for forming a first fold, said apparatus further comprising a second folding tool and second drive means for said second folding tool identical to said first mentioned drive means (6), said second folding tool being arranged to perform a folding motion substantially horizontally for forming a second fold.

16. The apparatus of claim 1, wherein said first rotation axis (24) of said driven shaft (20a), coincides with a central axis of said stationary sun gear (19), and wherein said second rotation axis (29) of said planetary gear (22) coincides with a rotation axis (25) of said mounting means (25, 26).

* * * * *

UNITED STATES PATENT AND TRADEMARK OFFICE
CERTIFICATE OF CORRECTION

PATENT NO. : 5,176,615

DATED     : January 5, 1993

INVENTOR(S) : Klaus Munsch

It is certified that error appears in the above-identified patent and that said Letters Patent is hereby corrected as shown below:

Column 9, line 34, replace "arm" by --drum--;

Column 9, line 38, replace "all" by --wall--.

Signed and Sealed this

Nineteenth Day of October, 1993

Attest:

BRUCE LEHMAN

Attesting Officer     Commissioner of Patents and Trademarks